US009735530B2

(12) United States Patent
Arceneaux et al.

(10) Patent No.: US 9,735,530 B2
(45) Date of Patent: Aug. 15, 2017

(54) APPARATUS AND METHOD FOR AXIALLY SPACING CONDUCTIVE RINGS OF A SLIP RING ASSEMBLY

(71) Applicant: General Electric Company, Schenectady, NY (US)

(72) Inventors: Mario Joseph Arceneaux, Simpsonville, SC (US); Kurt Kramer Schleif, Greenville, SC (US); Donald W. Shaw, Simpsonville, SC (US)

(73) Assignee: General Electric Company, Schenectady, NY (US)

( * ) Notice: Subject to any disclaimer, the term of this patent is extended or adjusted under 35 U.S.C. 154(b) by 377 days.

(21) Appl. No.: 14/643,242

(22) Filed: Mar. 10, 2015

(65) Prior Publication Data

US 2016/0268752 A1    Sep. 15, 2016

(51) Int. Cl.
| | |
|---|---|
| *G01R 27/04* | (2006.01) |
| *H01R 39/64* | (2006.01) |
| *H01R 13/6473* | (2011.01) |
| *H01R 39/08* | (2006.01) |
| *G01N 22/00* | (2006.01) |
| *H01R 43/10* | (2006.01) |

(52) U.S. Cl.
CPC ............ *H01R 39/64* (2013.01); *G01N 22/00* (2013.01); *H01R 13/6473* (2013.01); *H01R 39/08* (2013.01); *H01R 43/10* (2013.01)

(58) Field of Classification Search
CPC ........ G01N 22/00; G01N 17/00; G01N 24/00; G01R 27/26; G01R 27/2605
See application file for complete search history.

(56) References Cited

U.S. PATENT DOCUMENTS

| | | | |
|---|---|---|---|
| 3,711,942 | A | 1/1973 | Reynolds |
| 5,231,374 | A | 7/1993 | Larsen et al. |
| | | (Continued) | |

FOREIGN PATENT DOCUMENTS

EP    1748523    11/2009

OTHER PUBLICATIONS

Notice of Allowance issued in connection with related U.S. Appl. No. 14/543,944 on Dec. 1, 2015.

(Continued)

*Primary Examiner* — Tung X Nguyen
*Assistant Examiner* — Dominic C Hawkins
(74) *Attorney, Agent, or Firm* — Dority & Manning, P.A.

(57) ABSTRACT

An apparatus for determining axial spacing between conductive rings of a slip ring assembly includes a signal generator that generates an incident signal, a plurality of conductive rings axially spaced along a shaft where the plurality of conductive rings includes a first conductive ring and a second conductive ring that are axially spaced at a first axial distance. The shaft and the plurality of conductive rings are submerged in a bath of a liquid or encased in an epoxy. A first twisted wire pair is electronically coupled at to the signal generator and to inputs of the first and second conductive rings. A second twisted wire pair is electronically coupled at one end to outputs of the first and second conductive rings. A method for determining axial spacing between conductive rings of a slip ring assembly is also disclosed.

21 Claims, 4 Drawing Sheets

(56) References Cited

U.S. PATENT DOCUMENTS

| | | | | |
|---|---|---|---|---|
| 5,866,967 | A * | 2/1999 | Sasaki | H01R 39/646 310/11 |
| 5,952,762 | A * | 9/1999 | Larsen | B60R 16/027 310/232 |
| 6,472,791 | B1 * | 10/2002 | Rehder | H01F 38/18 310/129 |
| 7,019,431 | B1 * | 3/2006 | Kerlin | H01R 39/646 310/232 |
| 8,376,757 | B2 * | 2/2013 | Yamamoto | H01R 13/6473 439/18 |
| 8,629,588 | B2 * | 1/2014 | Park | H02K 53/00 310/58 |
| 9,240,660 | B1 * | 1/2016 | Arceneaux | F01D 17/02 |
| 2004/0161950 | A1 | 8/2004 | Coleman | |
| 2009/0320279 | A1 * | 12/2009 | Jayko | H02K 15/0006 29/732 |
| 2010/0225112 | A1 * | 9/2010 | Hayakawa | H02K 3/28 290/43 |
| 2012/0169176 | A1 * | 7/2012 | Toledo | H01R 39/42 310/240 |
| 2013/0200626 | A1 * | 8/2013 | Sidenmark | F03B 13/1885 290/53 |
| 2014/0055153 | A1 * | 2/2014 | Sato | G01R 31/34 324/750.3 |

OTHER PUBLICATIONS

Extended European Search Report and Opinion issued in connection with corresponding EP Application No. 16159152.4 on Aug. 5, 2016.
U.S. Appl. No. 14/543,944, Nov. 18, 2014, Arceneaux et al.
Technical Information, Moog Components Group. pp. 188-192; www.moog.com/components.
Aeroflex Airflyte, Basic Slip Ring Design Guide;www.aeroflex.com/Motion.
Co-pending U.S. Appl. No. 14/543,944, filed Nov. 18, 2014.

* cited by examiner

APPARATUS AND METHOD FOR AXIALLY SPACING CONDUCTIVE RINGS OF A SLIP RING ASSEMBLY

FIELD OF THE INVENTION

The present invention generally involves an apparatus and method for determining axial spacing between conductive rings of a slip ring assembly.

BACKGROUND OF THE INVENTION

Turbomachines such as wind turbines, gas turbines, steam turbines, pumps, fans, generators, motors, and other forms of commercial equipment frequently include shafts, blades, and other rotating components. It is known in the art to install one or more sensors on the rotating components to measure various characteristics of those components in order to control, monitor, and/or enhance the operation of the rotating components. For example, sensors that measure temperature, velocity, stress, strain, vibrations, and/or other characteristics of the rotating components may allow for early detection of abnormalities, adjustments to repair or maintenance schedules, and/or other actions to enhance operations.

Various contact type slip ring systems are known in the art for transmitting the analogue sensor data from the rotating components to stator components for further analysis and/or for transmitting power to or from a rotatable portion of the slip ring assembly. Conventionally, analogue signals from the sensors are routed via transmission lines (i.e. wires) to individual conductive rings of a slip ring assembly. The conductive rings are concentrically positioned along a rotatable center bore or shaft portion of the slip ring assembly. Stationary contact arms or brushes provide a signal path for routing the signals from the conductive rings to a stationary device such as a controller, data processor or the like. The corresponding concentric conductive rings are generally formed with a cross-section shape that may include grooves, slots and/or generally flat or arcuate surfaces that are appropriate for the sliding contact.

In order to accommodate ever increasing data requirements for test and operation of the turbomachine, it is often necessary to transmit high frequency signals such as digitized analogue signals from the sensors to the stationary device via the conductive rings. However, maximum transmission rate across the conductive ring may be limited by various factors.

One potential limiting factor is distortion of the waveforms due to reflections from electrical impedance discontinuities. Impedance discontinuities can occur throughout the slip ring assembly wherever different forms of transmission lines and components interconnect and that have different surge impedances. For example, high-frequency signal losses and/or degradation at the conductive rings may increase with signal frequency due to multiple reflections from impedance mismatches. Some of the highest incidences of impedance mismatches often occur where transmission lines such as a twisted wire pair from the sensors connect at a conductive ring and/or at the brush-conductive ring interface of a slip ring assembly and/or at connector interfaces.

Typically, impedance mismatches may be mitigated by increasing or decreasing the contact surface area (i.e. the width) of the conductive rings that carry high-frequency signals. However, this methodology may limit the number of conductive rings allowed along a given axial length of the center shaft due to limited axial space provided along a center bore of shaft portion of a slip ring assembly. As a result the number of digital transmissions that may be utilized, particularly in cases where overall axial length of the slip ring assembly is at issue, may be limited. Therefore, an apparatus and method for determining axial spacing between conductive rings of a slip ring assembly that provides for constant or substantially constant impedance across the slip ring assembly would be useful.

BRIEF DESCRIPTION OF THE INVENTION

Aspects and advantages of the invention are set forth below in the following description, or may be obvious from the description, or may be learned through practice of the invention.

One embodiment of the present invention is an apparatus for determining axial spacing between conductive rings of a slip ring assembly. The apparatus includes a signal generator that generates an incident signal, a signal generator that generates an incident signal, a shaft having a plurality of concentrically aligned conductive rings that are axially spaced along the shaft where the plurality of conductive rings comprises a first conductive ring axially spaced at a first axial distance from a second conductive ring. The shaft and the plurality of conductive rings are submerged in a bath of a liquid or encased in an epoxy. A first twisted wire pair is electronically coupled at one end to the signal generator and electronically coupled at a second end to inputs of the first and second conductive rings. A second twisted wire pair is electronically coupled at one end to outputs of the first and second conductive rings.

Another embodiment of the present invention is a method for determining axial spacing between conductive rings of a slip ring assembly. The method includes transmitting a first incident signal via a signal generator across a first conductive ring and a second conductive ring of a plurality of conductive rings via a first twisted wire pair that is electronically coupled to inputs of the first and second conductive rings and a second twisted wire pair that is electronically coupled to outputs of the first and second conductive rings. The first and second conductive rings are axially spaced along a shaft at a first axial distance. The plurality of conductive rings are submerged in a bath of a liquid or encased in an epoxy. The method also includes monitoring at the signal generator for signal reflections of the first incident signal where the signal reflections are indicative of impedance change through at least one of the first twisted wire pair, across the first or second conductive rings or through the second wire pair. The method may be repeated using other pairs of conductive rings of the plurality of conductive rings axially spaced at different axial distances until a desired signal reflection value is achieved.

Those of ordinary skill in the art will better appreciate the features and aspects of such embodiments, and others, upon review of the specification.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in that.

DETAILED DESCRIPTION OF THE INVENTION

Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

Although exemplary embodiments of the present invention will be described generally in the context of one type of slip ring assembly configured for transmitting digitized signals at relatively high frequencies for purposes of illustration, one of ordinary skill in the art will readily appreciate that embodiments of the present invention may be applied to any slip ring assembly for transmitting data, control or other signals or power from or to various electronics and/or sensors coupled to a rotating shaft.

Figure 1:
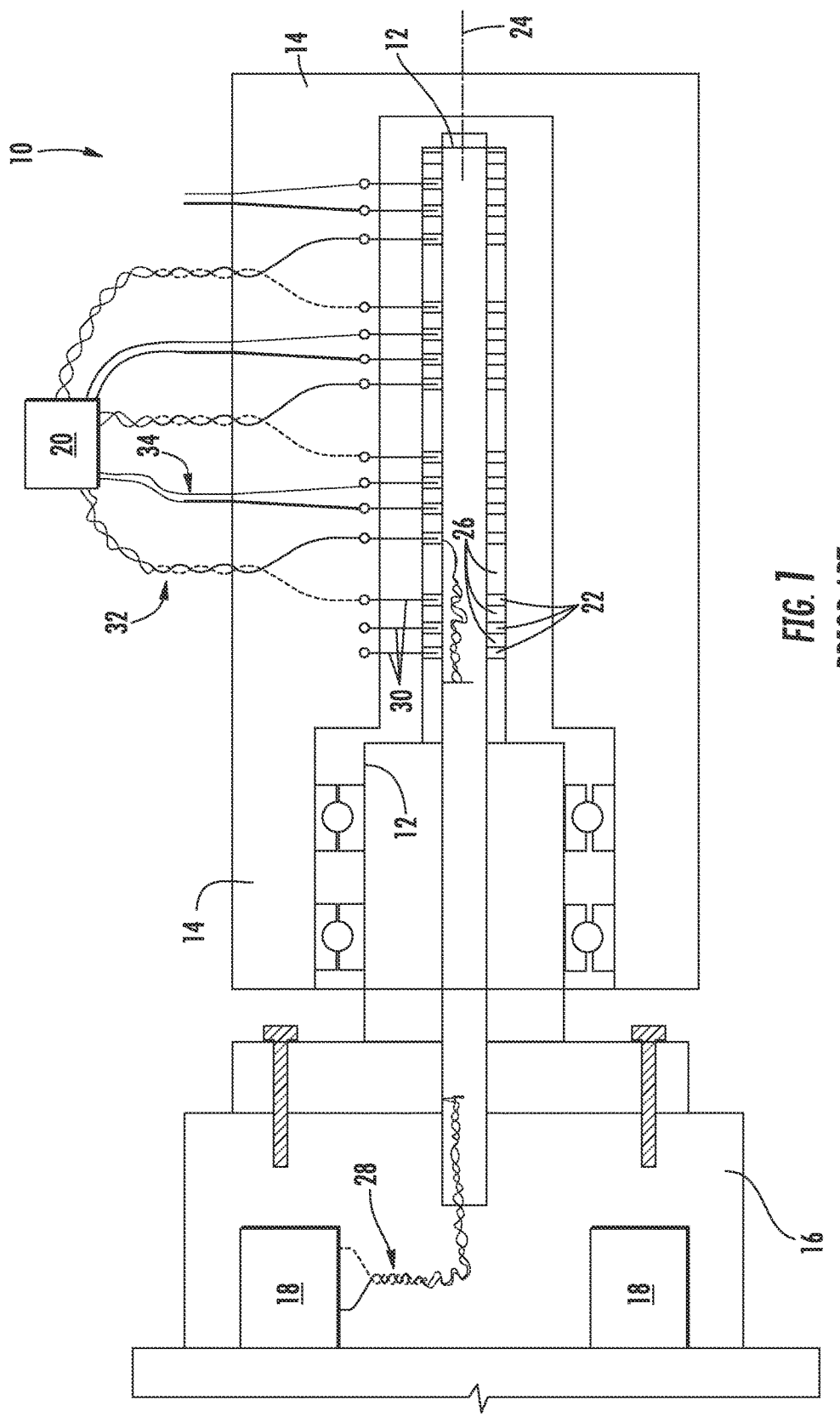
FIG. 1 is a partial cut away side view of a portion of an exemplary slip ring assembly as may incorporate one or more embodiments of the present invention.

Referring now to the drawings, wherein identical numerals indicate the same elements throughout the figures, FIG. 1 provides a functional block diagram of an exemplary slip ring assembly 10. In particular embodiments, as shown in FIG. 1, the slip ring assembly 10 generally includes a rotatable center shaft 12 that is circumferentially surrounded by a stator or stationary portion 14. The center shaft 12 may be configured to couple at one end to a rotor shaft 16 such as a rotor shaft of a gas turbine.

In various embodiments, an analog to digital convertor 18 may be disposed within the rotor shaft 16. The analog to digital convertor 18 may be electronically coupled to various sensors such as thermocouples (not shown) that are coupled to one or more rotating components attached to the rotor shaft 16. The analog to digital convertor 18 digitizes the analog signals from the sensors into digitized high frequency signals which are transmitted to the slip ring assembly 10 and on to a stationary controller or data acquisition unit 20.

The slip ring assembly also includes a plurality of conductive rings 22 concentrically aligned and axially spaced along the center shaft 12 with respect to an axial centerline 24 thereof. At least some of the conductive rings 22 may transfer analog and high frequency digital signals from the sensors and/or digital electronics through the slip ring assembly 10 and on to the data processor 20. At least some of the conductive rings 22 may be used to transfer power to the analog to digital convertor 18 or other devices electronically downstream from the center shaft 12. Each conductive ring 22 is axially separated from adjacent conductive rings 22 by an electrically insulating material 26. At least some of the conductive rings 22 may be electronically coupled to the analogue to digital convertor via wires 28.

Multiple brushes or contact members 30 are fixedly connected to the stator portion 14 of the slip ring assembly 10. Each contact member 30 is axially aligned with a corresponding conductive ring 22 and is configured to slideably engage with the corresponding conductive ring 22, thus defining a signal or current path between the two components. In various embodiments, the contact members 30 are electronically coupled to the data processor 20 and/or a power supply (not shown) via multiple wires or wire pairs 32, 34. Impedance matching of the signals between the sensors and the data processor 20, particularly with regards to digitized or high frequency digital signals provided by the analog to digital converter 18, is critical for reducing signal noise and/or corruption of the signals that may result from high-speed signal reflections from impedance discontinuities/mismatches along the signal path defined therebetween.

Figure 2:
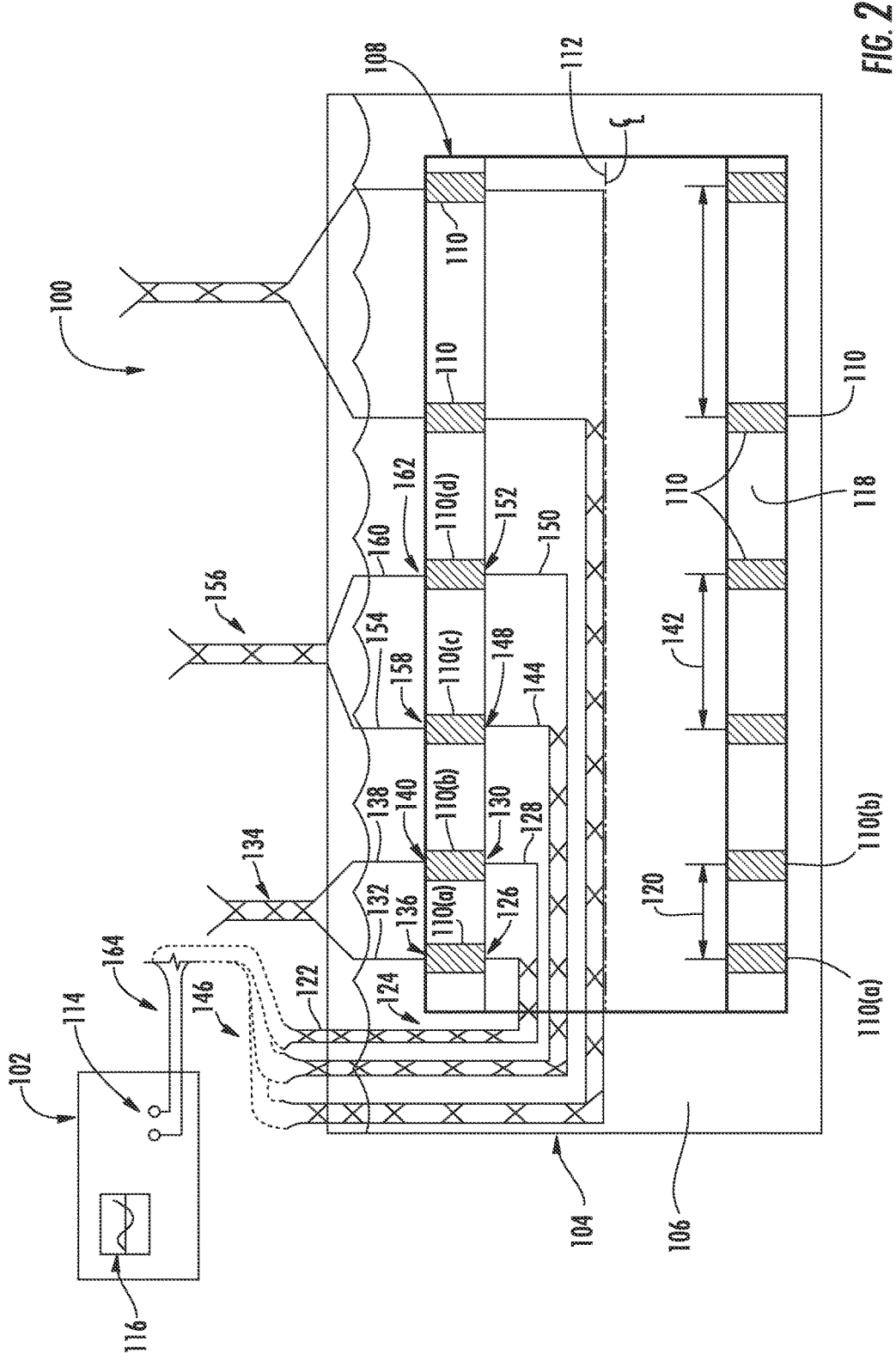
FIG. 2 is an enlarged view of a portion of an apparatus for determining axial spacing between conductive rings of a slip ring assembly, according to at least one embodiment of the present invention.
Figure 3:
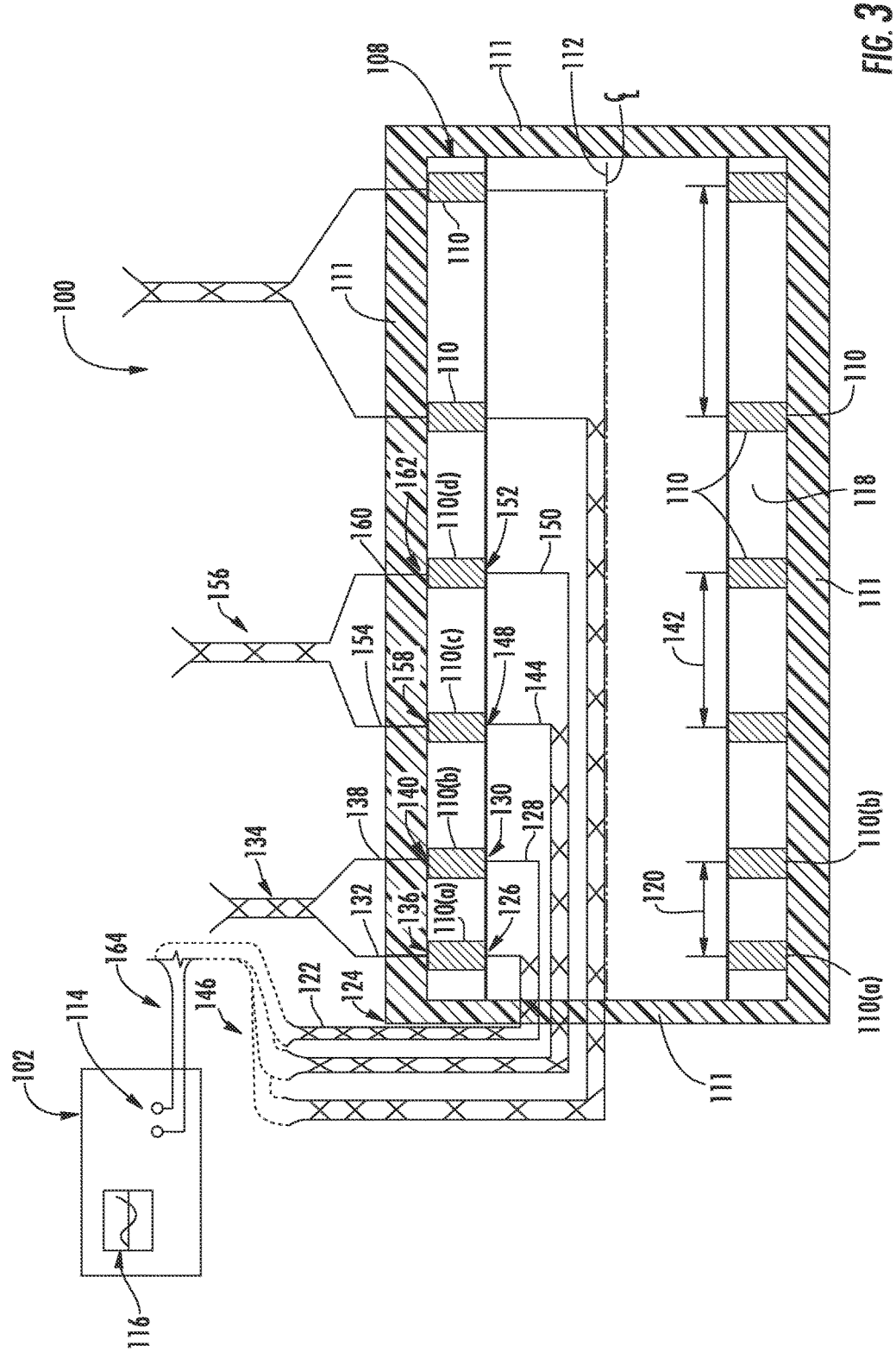
FIG. 3 is an enlarged view of a portion of an apparatus for determining axial spacing between conductive rings of a slip ring assembly, according to at least one embodiment of the present invention.
Figure 4:
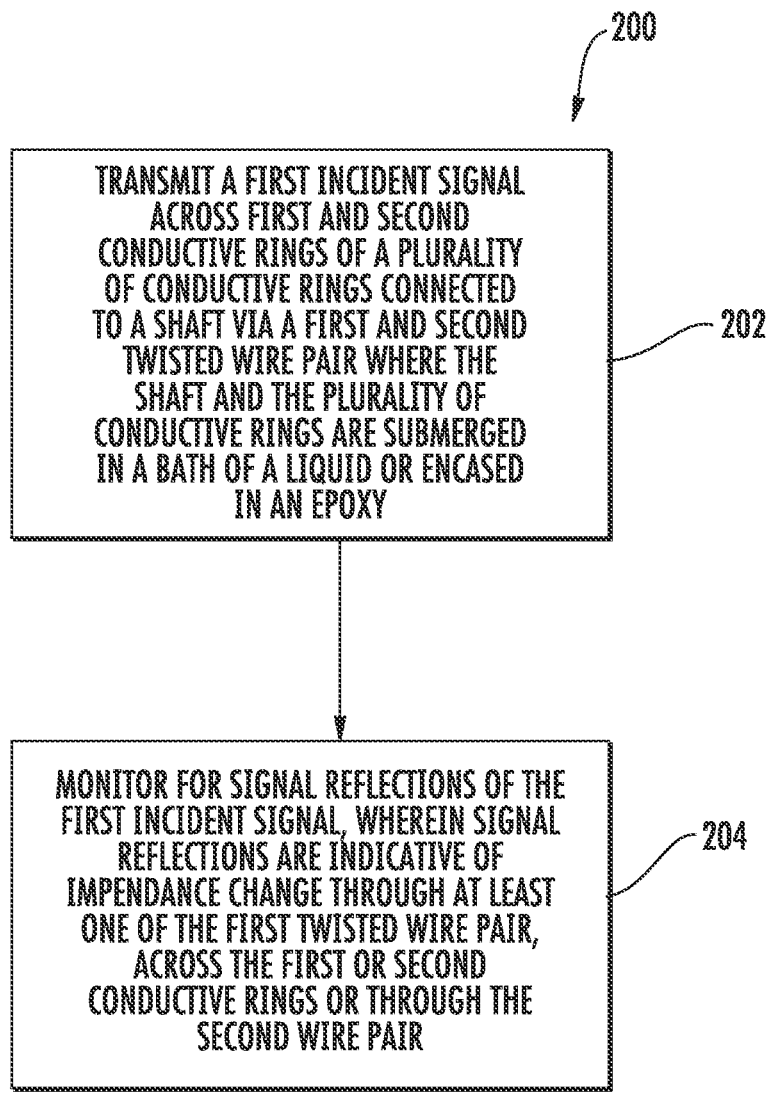
FIG. 4 is a block diagram of an exemplary method for determining axial spacing between conductive rings of a slip ring assembly.

FIGS. 2 and 3 each provide at least one embodiment of an apparatus 100 for determining axial spacing between conductive rings of a for impedance matching high-frequency signals through a slip ring assembly 10. The apparatus 100 as described and claimed herein may be used to determine an appropriate or required axial spacing between conductive rings of a slip ring assembly 10, such as shown in FIG. 1, and/or appropriate wiring so as to provide for constant impedance, particularly for high frequency signals, through the slip ring assembly. In various embodiments, the apparatus 100 includes a signal generator 102. In one embodiment, as shown in FIG. 1, the apparatus 100 includes a bath or container 104 that is at least partially filled with a liquid 106. The apparatus also includes a shaft 108 having a plurality of concentrically aligned conductive rings 110 axially spaced along the shaft 108 with respect to an axial centerline 112 of the shaft 108. In particular embodiments, as shown in FIG. 3, the plurality of conductive rings 110 are encased within an epoxy 111. The axial distance between the conductive rings 110 may be measured from outer edges, inner edges or a center (as shown) of the conductive rings 110.

In various embodiments, the signal generator 102 includes a signal output terminal 114. In particular embodiments, the signal generator 102 includes a display 116. The display 116 may include a graphical and/or a numerical display. In particular embodiments, the signal generator 102 is configured to generate and transmit an incident signal and to receive/measure reflections of the incident signal along a conductor such as a wire and/or a conductive ring via the output terminal 114. In various embodiments, the signal generator 102 comprises a Time-Domain Reflectometer. Time-Domain Reflectometers are commercially available such as the MOHR CT100 Series TDR Cable Tester sold commercially by MOHR, L.L.C. (Richland, Wash.).

The shaft 108 may be formed from a material having identical or substantially the same electrical properties of a center shaft 12 of a slip ring assembly 10, for example, as shown FIG. 1. In particular embodiments the shaft 108 has an identical or substantially the same dielectric constant as the center shaft 12. The shaft 108 and/or the conductive rings 100 may be sized and/or shaped to the same or substantially the same specifications of a center shaft and/or conductive rings for a slip ring assembly. In particular embodiments, at least some of the conductive rings 110 are axially separated from adjacent conductive rings 110 via an electrically insulating material 118. The electrically insulating material 118 may include an epoxy 111 that is suitable for prolonged operation in a high temperature environment. I various embodiments, the conductive rings 110 have a constant impedance. In particular embodiments, the constant impedance of the conductive rings 110 is between 50 ohms and 150 ohms. In one embodiment, the constant impedance of the conductive rings 110 is 100 ohms. In one embodiment, the constant impedance of the conductive rings 110 is 125 ohms.

In one embodiment, a first conductive ring 110(a) of the plurality of conductive rings 110 is axially spaced at a first axial distance 120 from a second conductive ring 110(b) with respect to centerline 112. A first wire 122 of a first twisted wire pair 124 is electronically coupled at one end of the first twisted wire pair 122 to an input 126, of the first conductive ring 110(a) and a second wire 128 of the first twisted wire pair 124 is electronically coupled to an input 130 of the second conductive ring 110(b). The first twisted wire pair 124 has a constant impedance. The constant impedance of the first twisted wire pair 124 may be the same or substantially the same as the constant impedance of the first conductive ring 110(a). In particular embodiments, the constant impedance of the first twisted wire pair 124 is between 50 ohms and 150 ohms. In one embodiment, the constant impedance of the first twisted wire pair 124 is 100 ohms. In one embodiment, the constant impedance of the first twisted wire pair 124 is 125 ohms.

A first wire 132 of a second twisted wire pair 134 is electronically coupled at one end of the second twisted wire pair 134 to an output 136 of the first conductive ring 110(a). A second wire 138 of the second twisted wire pair 134 is electronically coupled to an output 140 of the second conductive ring 110(b). The second twisted wire pair 134 has a constant impedance. The constant impedance of the second twisted wire pair 134 may be the same or substantially the same as the constant impedance of the first conductive ring 110(a). The constant impedance of the second twisted wire pair 134 may be the same or substantially the same as the constant impedance of the first twisted wire pair 124. In particular embodiments, the constant impedance of the second twisted wire pair 134 is between 50 ohms and 150 ohms. In one embodiment, the constant impedance of the second twisted wire pair 134 is 100 ohms. In one embodiment, the constant impedance of the second twisted wire pair 134 is 125 ohms.

In one embodiment, a third conductive ring 110(c) of the plurality of conductive rings 110 is axially spaced at a second axial distance 142 from a fourth conductive ring 110(d) with respect to axial centerline 112. A first wire 144 of a third twisted wire pair 146 is electronically coupled at one end of the third twisted wire pair 146 to an input 148 of the third conductive ring 110(c). A second wire 150 of the third twisted wire pair 146 is electronically coupled to an input 152 of the fourth conductive ring 110(d). The third twisted wire pair 146 has a constant impedance. The constant impedance of the third twisted wire pair 146 may be the same or substantially the same as the constant impedance of the second conductive ring 110(b). In particular embodiments, the constant impedance of the third twisted wire pair 146 is between 50 ohms and 150 ohms. In one embodiment, the constant impedance of the third twisted wire pair 146 is 100 ohms. In one embodiment, the constant impedance of the third twisted wire pair 146 is 125 ohms.

A first wire 154 of a fourth twisted wire pair 156 is electronically coupled at one end of the fourth twisted wire pair 156 to an output 158 of the third conductive ring 110(c). A second wire 160 of the second twisted wire pair 156 is electronically coupled to an output 162 of the fourth conductive ring 110(d). The fourth twisted wire pair 156 has a constant impedance. The constant impedance of the fourth twisted wire pair 156 may be the same or substantially the same as the constant impedance of the second conductive ring 110(b). The constant impedance of the fourth twisted wire pair 156 may be the same or substantially the same as the constant impedance of the third twisted wire pair 146. In particular embodiments, the constant impedance of the fourth twisted wire pair 156 is between 50 ohms and 150 ohms. In one embodiment, the constant impedance of the fourth twisted wire pair 156 is 100 ohms. In one embodiment, the constant impedance of the fourth twisted wire pair 156 is 125 ohms.

It should be appreciated that the shaft 108 may include any number of the conductive rings 110 axially spaced at various axial distances along the shaft 108 and wired in pairs as illustrated and described with regards to conductive rings 110(a-d). In particular embodiments, each of the conductive rings 110 or at least some of the conductive rings 110 of the plurality of conductive rings 110 are similarly wired in pairs via twisted wire pairs.

In various embodiments, the first twisted wire pair 124 and the second twisted wire pair 146 have constant impedances that are substantially the same. In one embodiment, both the first twisted wire pair 124 and the second twisted wire pair 146 have the same or substantially the same impedance when submerged in a liquid such as olive oil and/or encased within an epoxy 111. In one embodiment, the first twisted wire pair 122 and the second twisted wire pair 134 have constant impedances of 125-ohms. In one embodiment, the third twisted wire pair 146 and the fourth twisted wire pair 156 have constant impedances of 125-ohms. In particular embodiments, the first twisted wire pair 122 and the second twisted wire pair 134 are 34AWG125-ohm twisted wire pairs. In particular embodiments, the third twisted wire pair 146 and the fourth twisted wire pair 156 are small gage twisted wire pairs such as 34AWG125-ohm twisted wire pairs.

In particular embodiments, the first twisted wire pair 124 and/or the third twisted wire pair 146 are electronically coupled to the terminal outputs 114 of the signal generator 102. In particular embodiments, the first twisted wire pair 124 and/or the third twisted wire pair 146 are electronically coupled to the terminal outputs 114 of the signal generator 102 via a LAN cable 164. In one embodiment, the LAN cable 164 is a CAT5e network cable. The first and second wires 132, 138 of the second twisted wire pair 134 and/or the first and second wires 154, 160 of the fourth twisted wire pair 156 may be left open or non-terminated.

In various embodiments, the shaft 108 including the plurality of conductive rings 110 is submerged in the liquid 106 held in the bath 104. In other embodiments, the shaft 108 including the plurality of conductive rings 110 is encased or within an epoxy 111. The liquid 106 has a predefined dielectric constant. In one embodiment, the liquid 106 has a dielectric constant equal to a glass-reinforced epoxy 111, such as an FR4 PCB material, at 125 degrees Celsius. In one embodiment, the liquid comprises a commercially available olive oil. In one embodiment, the olive oil is extra virgin olive oil which is also commercially available.

The apparatus 100 as illustrated in FIG. 2 and described herein, may be used to identify proper axial spacing between the conductive rings 110 and/or for selecting wires or wire pairs when designing or specifying a slip ring assembly so as to avoid, reduce or minimize impedance drops across the slip ring assembly. FIG. 3 provides a block diagram of an exemplary method 200 for determining axial spacing between conductive rings of a slip ring assembly. At 202, method 200 includes transmitting a first incident signal via the signal generator 102 across the first conductive ring 110(a) and the second conductive ring 110(b) of the plurality of conductive rings 110 via the first twisted wire pair 124 that is electronically coupled to the inputs 126, 130 of the first and second conductive rings 110(a), 110(b) and the second twisted wire pair 134 that is electronically coupled to the outputs 136, 140 of the first and second conductive rings 110(a), 110(b) where the first and second conductive rings 110(a), 110(b) are axially spaced along the shaft 108 at the first axial distance 120 and where the shaft 108 and the plurality of conductive rings 110 are submerged in a bath of a liquid or encased in an epoxy 111. At 204, method 200 includes monitoring at the signal generator 102 for signal reflections of the first incident signal where the signal reflections are indicative of impedance change through at least one of the first twisted wire pair 122, across the first or second conductive rings 110(a), 110(b) or through the second wire pair 134.

In one embodiment, wherein if signal reflections of the first incidental signal are detected, method 200 further comprises transmitting a second incident signal via the signal generator 102 across the third conductive ring 110(c) and the fourth conductive ring 110(d) of the plurality of conductive rings 110 via the third twisted wire pair 146 and the fourth twisted wire pair 156 where the third and fourth conductive rings 110(c-d) are axially spaced at the second axial distance 142. Method 200 further includes monitoring at the signal generator 102 for signal reflections of the second incident signal. If signal reflections are detected for the first and second incident signals, method 200 further comprises comparing signal reflection values from the first and second incident signals and choosing a desired axial spacing between the first and second axial distances 120, 142 based on the lowest signal reflection value.

In one embodiment of method 200, where the shaft 108 and the plurality of conductive rings 110 are submerged in the bath 104 of liquid 106, the liquid 106 has a dielectric constant that is equal to a glass-reinforced epoxy 111. In one embodiment of method 200, the liquid 106 has a dielectric constant that is equal to a FR2 PCB material. In one embodiment of method 200, the liquid 106 comprises olive oil. In one embodiment of method 200, the incident signal is generated via a time-domain reflectometer. In one embodiment of method 200, the first twisted wire pair 124 and the second twisted wire pair 134 have constant impedances that are substantially the same. In one embodiment of method 200, the first twisted wire pair 124 and the second twisted wire pair 134 are 34AWG125-ohm twisted wire pairs.

In one embodiment, where the first twisted wire pair 124 is electronically coupled to the signal generator 102 via the LAN cable 164, method 200 further includes calibrating the signal generator using a known impedance of the CAT5e network cable. In one embodiment, method 200 further includes transmitting a second incident signal via the signal generator 102 across the third conductive ring 110(c) and the fourth conductive ring 110(d) via the third twisted wire pair 146 that is electronically coupled to the input 148 of the third conductive ring 110(c) and the input 152 of the fourth conductive ring 110(d), and through the fourth twisted wire pair 156 that is electronically coupled to the outputs 158, 162 of the third and fourth conductive rings 110(c), 110(d) respectfully, where the third and fourth conductive rings 110(c), 110(d) are axially spaced along the shaft 108 at the second axial distance 142. The second axial distance 142 is greater than or less than the first axial distance 120.

In particular embodiments, method 200 further includes monitoring at the signal generator for signal reflections of the second incident signal, and wherein if signal reflections are detected for the first and second incident signals, the method 200 further comprises comparing signal reflection values from the first and second incident signals and choosing axial spacing of conductive rings for a slip ring assembly based, at least in part, on the lowest signal reflection value.

In one embodiment, the apparatus may be specifically used to for determining axial spacing between conductive rings of a slip ring assembly to achieve 100 ohm impedance through the slip ring assembly 10. The first and second twisted wire pairs 122, 134 and/or the third and fourth twisted wire pairs 146, 156 have a constant impedance of 125 ohms. This may be achieved by using 34AWG125-ohm twisted wire pairs for both the first and second twisted wire pairs 122, 134 and the third and fourth twisted wire pairs 146, 156. The twist of the first and second twisted wire pairs 122, 134 and/or the third and fourth twisted wire pairs 146, 156 is maintained as close as possible to the corresponding inputs 126, 130, 148, 152 and corresponding outputs 136, 140, 158, 162 of the corresponding conductive rings 110(a-d). The shaft 108 including the plurality of conductive rings 110, particularly conductive rings 110(a-d) is submerged in extra virgin olive or encased within the epoxy 111. The signal generator 102 is a time-domain reflectometer and is calibrated using a known impedance of the LAN cable 164 such as a CAT5e network cable. The second and fourth twisted wire pairs 134, 156 are left open or non-terminated.

The first twisted wire pair 124 is electronically coupled to the signal generator 102 via the CAT5e network cable 164. An incident signal is generated by the signal generator 102. The signal generator 102 monitors for signal reflections of the incident signal that are indicative of impedance mismatch along the first and second twisted wire pairs 124, 134 and/or the conductive rings 110(a-b). If there is no indication and/or an acceptable indication of an impedance mismatch or discontinuity, the axial spacing 120 between the conductive rings 110(a-b) will be specified for the slip assembly.

If impedance mismatch is detected, the third twisted wire pair 146 is electronically coupled to the signal generator 102 via the CAT5e network cable 164. An incident signal is generated by the signal generator 102. The signal generator 102 monitors for signal reflections of the incident signal that are indicative of impedance mismatch along the third and fourth twisted wire pairs 146, 156 and/or the conductive rings 110(c-d). If there is no indication and/or an acceptable indication of an impedance mismatch or discontinuity, the axial spacing 142 between the conductive rings 110(c-d) will be specified for the slip ring assembly. If impedance mismatch is detected, this process may be repeated until a suitable axial spacing is determined that provides a constant 100 ohm impedance through the corresponding twisted wire pairs and the corresponding conductive rings 110.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other and examples are intended to be within the scope of the claims if they include structural elements that do not differ from the literal language of the claims, or if they include equivalent structural elements with insubstantial differences from the literal languages of the claims.

What is claimed is:

1. An apparatus for determining axial spacing between slip rings for impedance matching high-frequency signals through a slip ring assembly, the apparatus comprising:
   a signal generator that generates an incident signal;
   a shaft having a plurality of concentrically aligned conductive rings axially spaced along the shaft, wherein the plurality of conductive rings comprises a first conductive ring axially spaced at a first axial distance from a second conductive ring, wherein the shaft and the plurality of conductive rings are submerged in a bath of a liquid or encased in an epoxy;
   a first twisted wire pair electronically coupled at one end to the signal generator and electronically coupled at a second end to inputs of the first and second conductive rings; and
   a second twisted wire pair electronically coupled at one end to outputs of the first and second conductive rings.

2. The apparatus as in claim 1, wherein the signal generator is configured to monitor for signal reflections of the incident signal.

3. The apparatus as in claim 1, wherein the signal generator is a time-domain reflectometer.

4. The apparatus as in claim 1, wherein the shaft and the plurality of conductive rings are submerged in a bath of a liquid, wherein the liquid comprises olive oil.

5. The apparatus as in claim 4, wherein the liquid has a dielectric constant equal to the dielectric constant of a glass-reinforced epoxy at 125 degrees Celsius.

6. The apparatus as in claim 4, wherein the liquid has a dielectric constant equal to a glass-reinforced epoxy.

7. The apparatus as in claim 1, wherein the liquid or the epoxy has a dielectric constant that is equal to a FR4 PCB material.

8. The apparatus as in claim 1, wherein the first twisted wire pair and the second twisted wire pair have constant impedances that are substantially the same.

9. The apparatus as in claim 1, wherein the first twisted wire pair and the second twisted wire pair have constant impedances of 125-ohms.

10. The apparatus as in claim 1, wherein the first and the second twisted wire pairs are 34AWG125-ohm twisted wire pairs.

11. The apparatus as in claim 1, wherein the first twisted wire pair is electronically coupled to the signal generator via a CAT5e network cable, wherein the signal generator is calibrated using a known impedance of the CAT5e network cable.

12. A method for determining axial spacing between conductive rings of a slip ring assembly, comprising:
   transmitting a first incident signal via a signal generator across a first conductive ring and a second conductive ring of a plurality of conductive rings via a first twisted wire pair that is electronically coupled to inputs of the first and second conductive rings and a second twisted wire pair that is electronically coupled to outputs of the first and second conductive rings, wherein the first and second conductive rings are axially spaced along a shaft at a first axial distance, wherein the shaft and the plurality of conductive rings are submerged in a bath of a liquid or encased in an epoxy; and
   monitoring at the signal generator for signal reflections of the first incident signal, wherein signal reflections are indicative of impedance change through at least one of the first twisted wire pair, across the first or second conductive rings or through the second wire pair.

13. The method as in claim 12, wherein if signal reflections of the first incidental signal are detected, the method further comprises:
   transmitting a second incident signal via the signal generator across a third conductive ring and a fourth conductive ring of the plurality of conductive rings via a third twisted wire pair that is electronically coupled to inputs of the third and fourth conductive rings and a fourth twisted wire pair that is electronically coupled to outputs of the third and fourth conductive rings, wherein the third and fourth conductive rings are axially spaced at a second axial distance; and
   monitoring at the signal generator for signal reflections of the second incident signal; and
   wherein if signal reflections are detected for the first and second incident signals, the method further comprising comparing signal reflection values from the first and second incident signals and choosing a desired axial spacing based on the lowest signal reflection value.

14. The method as in claim 12, wherein the shaft and the plurality of conductive rings are submerged in a bath of a liquid, wherein the liquid comprises olive oil.

15. The method as in claim 14, wherein the liquid has a dielectric constant equal to the dielectric constant of a glass-reinforced epoxy at 125 degrees Celsius.

16. The method as in claim 14, wherein the liquid has a dielectric constant equal to a glass-reinforced epoxy.

17. The method as in claim 12, wherein the liquid or the epoxy has a dielectric constant that is equal to a FR4 PCB material.

18. The method as in claim 12, wherein the incident signal is generated via a time-domain reflectometer.

19. The method as in claim 12, wherein the first twisted wire pair and the second twisted wire pair have constant impedances that are substantially the same.

20. The method as in claim 12, wherein the first twisted wire pair and the second twisted wire pair are 34AWG125-ohm twisted wire pairs.

21. The method as in claim 12, wherein the first twisted wire pair is electronically coupled to the signal generator via a CAT5e network cable, the method further comprising calibrating the signal generator using a known impedance of the CAT5e network cable.

* * * * *